US00PP13081P2

(12) United States Plant Patent
Crandall

(10) Patent No.: US PP13,081 P2
(45) Date of Patent: Oct. 15, 2002

(54) STRAWBERRY PLANT NAMED 'COLIMA'

(75) Inventor: Beth Crandall, Watsonville, CA (US)

(73) Assignee: Beach Street Farms, LLC, Watsonville, CA (US)

( * ) Notice: Subject to any disclaimer, the term of this patent is extended or adjusted under 35 U.S.C. 154(b) by 0 days.

(21) Appl. No.: 09/383,111

(22) Filed: Aug. 25, 1999

(51) Int. Cl.[7] ..... A01H 5/00
(52) U.S. Cl. ..... Plt./208
(58) Field of Search ..... Plt./208, 209

(56) References Cited

PUBLICATIONS

Grower Contract.
Nursery Contract 1.
Nursery Contract 2.
Nursery Contract 3.
Nursery Contract 4.
Field Agreement 1.
Field Agreement 2.
Field Agreement 3.
Field Agreement 4.
Greenhouse Agreement.

*Primary Examiner*—Bruce R. Campell
*Assistant Examiner*—Michelle Kizilkaya
(74) *Attorney, Agent, or Firm*—Townsend & Townsend & Crew LLP

(57) ABSTRACT

The present invention provides a new and distinct strawberry variety designated as 'Colima.' Among the characteristics that distinguish the new variety from other closely related varieties are the timing of fruiting, plant vigor, fruit color, leaf morphology, leaf size, leaf color, and disease and pest resistance.

2 Drawing Sheets

CROSS-REFERENCES TO RELATED APPLICATIONS

There are no related applications.

BACKGROUND OF THE INVENTION

The new strawberry variety claimed herein was first fruited in 1992 in a seedling field east of Highway 101 and North of Boranda Road in Salinas, Calif., where it was selected, designated 91711-503, and propagated asexually by runners. The new variety resulted from a cross performed between Parker (U.S. Plant Pat. No. 5,263) and Douglas (U.S. Plant Pat. No. 4,487). Asexually propagules from this original source have been tested at coastal and inland locations in Watsonville, Calif., and at one location in Oxnard, Calif. With the decision that this plant was to be released, it was given the variety name 'Colima' for the purposes of introduction into commerce and for international registration and recognition.

BRIEF SUMMARY OF THE INVENTION

The present invention relates to a new and distinct strawberry variety designated as 'Colima.' The cultivar is botanically identified as *Fragaria×ananassa* Duch. Among the characteristics that distinguish the new variety from other closely related varieties are the timing of fruiting, plant vigor, fruit color, leaf morphology, leaf size, leaf color, and disease and pest resistance.

DETAILED BOTANICAL DESCRIPTION

Figure 1:
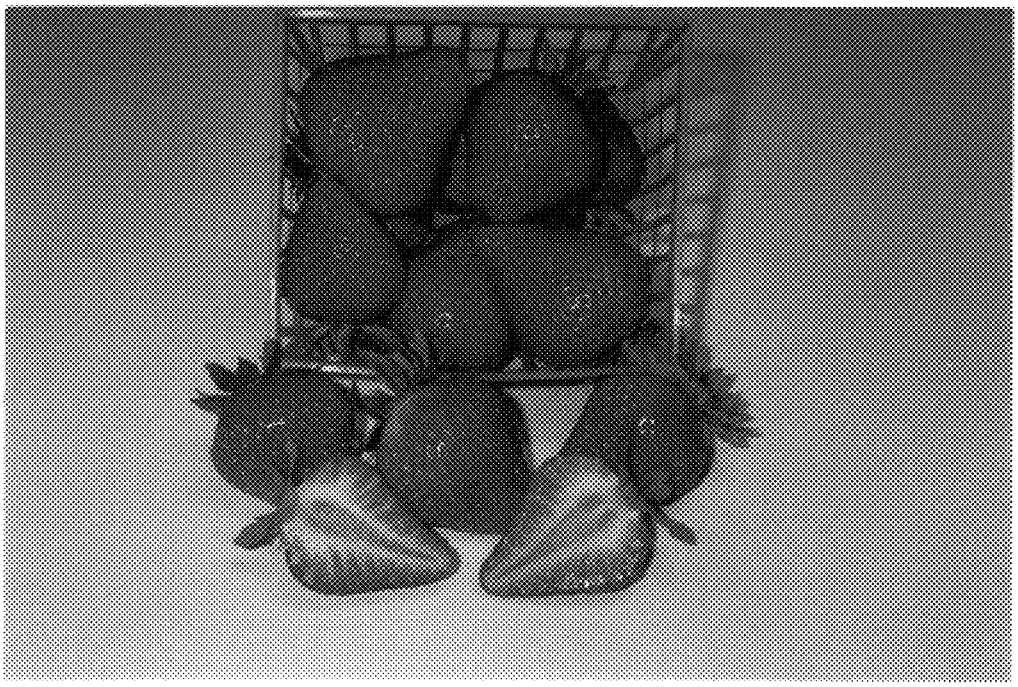
FIG. 1 depicts representative mid-season fruit.
Figure 2:
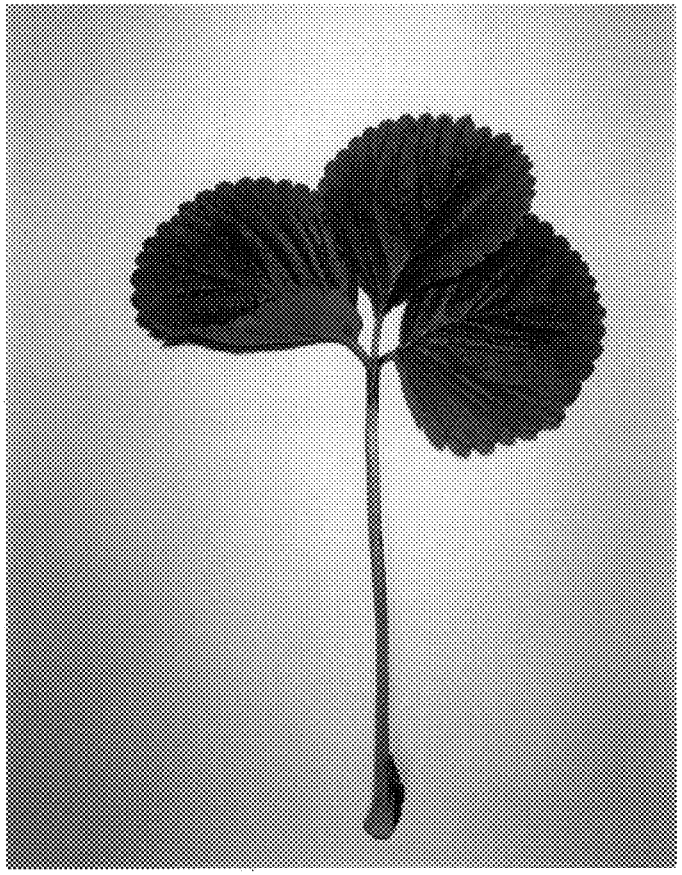
FIG. 2 depicts a typical mature leaf during late spring.
Figure 3:
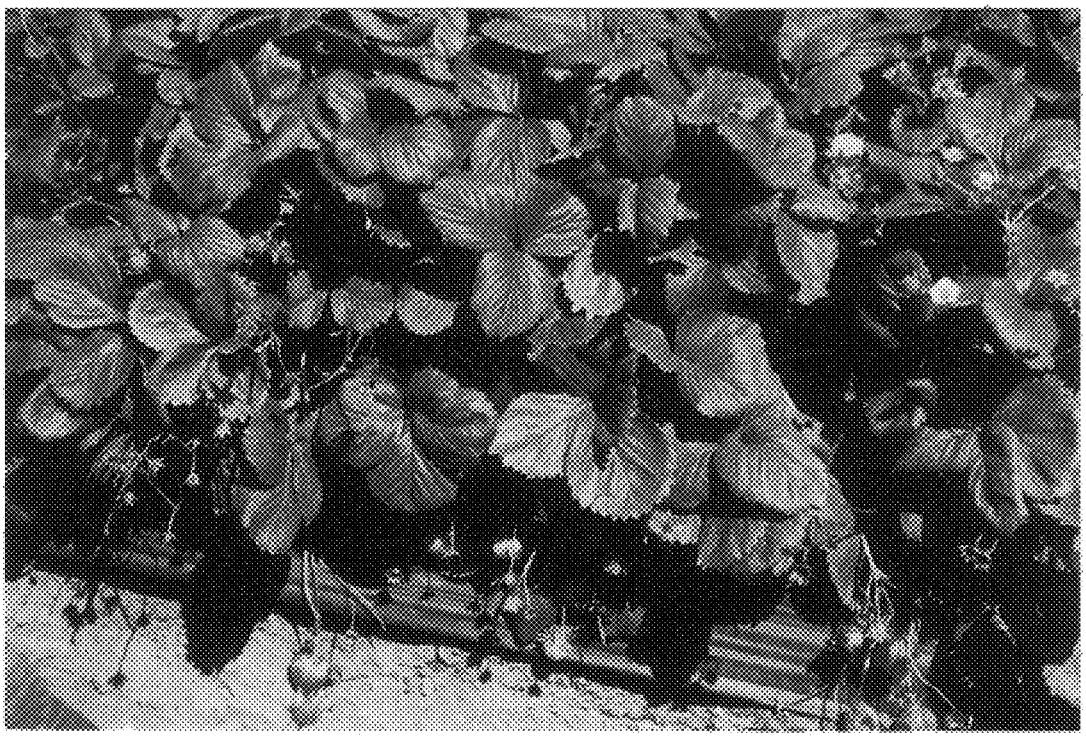
FIG. 3 depicts the general flowering and fruiting characteristics of the plant.

'Colima' is an early fruiting, weak day-neutral cultivar with shiny, deep red fruit that has performed well at coastal and inland areas in Watsonville, Calif., which is where the plants were observed for the following descriptions. 'Colima' has a large and moderately vigorous plant. Where it has been tested, it is competitive with the important cultivars grown in the area. 'Colima' fruits earlier than 'Selva' (U.S. Plant Pat. No. 5,266). The fruit of 'Colima' is slightly darker than 'Selva'. The following description is based on plants aged 7 to 9 months from planting. Descriptions of fruit characteristics are based on primary fruit.

Plants and Foliage

'Colima' has a larger plant type than 'Selva', with slightly thicker crowns, petioles and runners. The average plant height is 25 cm. The average plant spread is 45 cm. Plant vigor is moderate to good. Canopy density is moderate. Plants habit is semi prostrate. Bracts occur in pairs at 100% of the nodes. Leaf characteristics comparing 'Colima' and 'Selva' are reported in Table 1. Leaves of 'Colima' tend to be shorter and wider than those of 'Selva', with more variability in leaf size overall. Leaves of 'Colima' are more concave, while leaves of 'Selva' are more convex. 'Colima' produces more leaves per plant, resulting in a denser canopy of leaf material although leaves themselves are slightly thinner than 'Selva'. 'Colima' is a lighter colored plant than 'Selva' and can appear slightly yellow at times during the season. Leaf color (using Munsell color charts) is reported in Table 2. Characteristics of petioles, peduncles, and pedicels are set forth in Table 3.

The average number of stolons is between 0.5 and 1 stolon per plant. The stolons are 15 to 25 cm in length and 3 to 6 mm in diameter. The pubescence is sparse to moderate. The stolons contain a small to moderate amount of anthocyanin and are light pink in color.

Isozymes in Leaf Extracts

'Colima' has been classified for three isozyme systems, using starch gel eletrophoresis. Electrophoresis was carried out according to standard techniques. The following enzymes were analyzed: phosphoglocoisomerase (PGI), leucine aminopeptidase (LAP), and phosphoglucomutase (PGM). 'Colima' and 'Selva' share the same PGI, LAP and PGM phenotypes as shown in Table 4.

Disease and Pest Reaction

Disease and pest reactions of 'Colima' and 'Selva' were observed in field situations in Watsonville and in the Northern California nurseries. Neither cultivar was artificially inoculated. 'Colima' showed higher tolerance to two spotted spider mites (*Tetranychus urticae*) than 'Selva'. However, slightly higher levels of Powdery Mildew (*Sphaerotheca macularis*) were seen in 'Colima' than were seen in 'Selva'.

Flowering, Fruiting and Production Characteristics

'Colima' is a day-neutral cultivar. However, 'Colima' is not as strong a day-neutral as 'Selva'. As is typical of the species, the flowers are perfect; petals are pure white and are rounded and entire; and anthers and receptacle are bright yellow. The distinguishing flower characteristics of 'Colima' as compared to 'Selva' are shown in Table 5. One of the most distinctive differences is that 'Colima' produces floral structures that are less exposed than those of 'Selva'. The petals are 9–13 mm in diameter. Sepals are 16–22 mm long and 6–12 mm wide.

The flowers of 'Colima' are self-fertile and pollination is very good. When plants are produced in nurseries in Northern California and planted in November, they typically begin to flower in late February or early March and fruit begin to mature four to six weeks later. 'Colima' produces a large number of runners at the nursery, with high quality root systems. The fruit of 'Colima' has excellent color, bright shiny red to dark red with yellow to brown seeds. The interior color of 'Colima' fruit is red with some white veining. The fruit of 'Colima' tends to be blocky and somewhat ridged, with smaller fruit having solid centers and larger fruit having a hollowing in the center. Fruit size of 'Colima' is initially larger than that of 'Selva', but over the season the fruit size of 'Colima' is variable with smaller fruit later in the season. The fruit of 'Colima' is almost as firm as that of 'Selva' with a flavor that is slightly more acidic. The calyx adhesion to fruit is good. The length of the fruiting trusses is 13–25 cm, their attitude is 45°–60° raised above horizontal. Average Fruit length is 49 mm and average width is 44 mm across the shoulders. Sugar content is variable and is influenced by time of year, carbohydrate distribution, leaf area, sunlight, moisture, ripeness, pests and diseases, and physiological status of the plant. Berries per plant is 80–100 berries over the season. Average weight of the berries is 23 gm. Achenes are present.

'Colima' begins to fruit earlier in the season than 'Selva' and has higher overall yields. In 'Colima' there is very heavy fruit production from April through July, after which fruit production decreases but continues into October and early November. Production yield is 100 mt/ha total fruit. 'Colima' is recommended as a fresh market cultivar although it can be used for processing.

TABLE 1

Foliar Characteristics for 'Colima' and 'Selva'

| Foliar Character | Cultivar 'Colima' | Cultivar 'Selva' |
|---|---|---|
| Mid-tier leaflet Length (mm) | | |
| mean | 75.6 | 72.6 |
| range | 45–95 | 65–88 |
| Mid-tier leaflet Width (mm) | | |
| mean | 67.3 | 68.2 |
| range | 44–80 | 51–84 |
| Mid-tier leaf Length (mm) | | |
| mean | 93.5 | 119.2 |
| range | 60–110 | 94–139 |
| Mid-tier leaf Width (mm) | | |
| mean | 142.2 | 130.1 |
| range | 90–150 | 111–170 |
| # of leaflets/leaf | 3 | 3 |
| Leaf Convexity | flat to concave | mostly flat to convex |
| Leaf Serrations | | |
| number | moderate | few-moderate |
| shape | semi round | round to semi-pointed |
| Leaf Pubescence | sparse to moderate | moderate |
| Petiole Pubescence | sparse to moderate | heavy |

TABLE 2

Foliar and fruit color characteristics for 'Colima' and 'Selva'

| Character | Cultivar 'Colima' | Cultivar 'Selva' |
|---|---|---|
| Leaf Color Adaxial | 5GY 4/6 | 7.5GY 4/4 |
| Leaf Color Abaxial | 5GY 5/8 | 2.5G 3/3 |
| External Fruit Color | 5R 4/12 | 5R 4/12 |
| Internal Fruit Color | 5R 5/8 | 5R 5/13 |

All color From the Munsell Color System

TABLE 3

Characteristics of Petioles, Peduncles, and Pedicels

| | Munsell Color | Length (cm) | Widths (mm) | Average Number |
|---|---|---|---|---|
| Petioles | 5GY 7/6 | 7.5–20 | 1.5–5 | 24.6 |
| Peduncles | 5GY 7/6 | 10–18 | 3–6 | 8.2 |
| Pedicels | 5GY 7/6 | 1–6 | 1.5–3 | 80 |

TABLE 4

Isozyme phenotypes for 'Colima' and 'Selva'

| Locus | Cultivar 'Colima' | Cultivar 'Selva' |
|---|---|---|
| PGI | A2 | A2 |
| LAP | B3 | B3 |
| PGM | C2 | C2 |

TABLE 5

Flower and Fruit Characters for 'Colima' and 'Selva'

| Character | Cultivar 'Colima' | Cultivar 'Selva' |
|---|---|---|
| Number of Petals | | |
| mean | 6.2 | 5.8 |
| range | 5–8 | 5–8 |
| Flower position (relative to foliage) | most even or interior few exposed | even or interior |
| Calyx Diameter (mm) | | |
| mean | 39.36 | 29 |
| range | 33–53 | 22–35 |
| Corolla Diameter (mm) | | |
| mean | 36.9 | 37.5 |
| range | 27–46 | 31–43 |

TABLE 5-continued

Flower and Fruit Characters for 'Colima' and 'Selva'

| Character | Cultivar 'Colima' | Cultivar 'Selva' |
|---|---|---|
| Fruit shape (length to width) | | |
| ratio | 1.11 | 1.16 |
| range | 0.9–1.5 | 1.02–1.25 |
| subjective | blocky to conic | conic to flat conic |
| Calyx Position | even some relexed | even with shoulder |
| Seed Position | even | even to slightly extruded |

What is claimed is:

1. The new and distinct cultivar of strawberry plant substantially as herein described and illustrated.

* * * * *